United States Patent
Nagata et al.

(10) Patent No.: US 10,293,123 B2
(45) Date of Patent: May 21, 2019

(54) TEST SUBSTANCE ADMINISTRATION SYSTEM FOR ANIMAL EXPERIMENT

(75) Inventors: Ryoichi Nagata, Kagoshima (JP); Tatsuo Tsutsui, Yokohama (JP); Shunji Haruta, Kagoshima (JP)

(73) Assignee: Shin Nippon Biomedical Laboratories, Ltd. (JP)

( * ) Notice: Subject to any disclaimer, the term of this patent is extended or adjusted under 35 U.S.C. 154(b) by 502 days.

(21) Appl. No.: 12/600,831

(22) PCT Filed: May 23, 2007

(86) PCT No.: PCT/JP2007/060521
§ 371 (c)(1),
(2), (4) Date: Jun. 30, 2010

(87) PCT Pub. No.: WO2008/142786
PCT Pub. Date: Nov. 27, 2008

(65) Prior Publication Data
US 2010/0263666 A1 Oct. 21, 2010

(51) Int. Cl.
*A61M 15/00* (2006.01)
*A61D 7/04* (2006.01)
*A61M 16/00* (2006.01)

(52) U.S. Cl.
CPC ........ *A61M 15/00* (2013.01); *A61M 15/0005* (2014.02); *A61D 7/04* (2013.01);
(Continued)

(58) Field of Classification Search
CPC ...... A61M 11/00; A61M 11/02; A61M 11/04; A61M 11/06; A61M 11/08; A61M 15/00;
(Continued)

(56) References Cited

U.S. PATENT DOCUMENTS 1,308,599 A * 7/1919 Luchs .................... 128/204.28
3,809,084 A * 5/1974 Hansen ................. A61M 15/00
                                                    128/203.15
(Continued)

FOREIGN PATENT DOCUMENTS

JP   51-27582 A   3/1976
JP   2-215464 A   8/1990
(Continued)

OTHER PUBLICATIONS

International search report dated Jul. 3, 2007 for PCT Application No. JP2007/60521.

*Primary Examiner* — Michael J Tsai
(74) *Attorney, Agent, or Firm* — Wilson, Sonsini, Goodrich & Rosati, P.C.

(57) ABSTRACT

[Subject]
A test substance application system for animal experiment capable of administering a required amount of a test substance uniformly and reliably from a nose or a mouth into a nasal cavity or into a lung of an experimental animal is provided.
[Means for Solution]
The system includes a respiration monitoring device 2 that monitors a respiration state of an experimental animal detected by a respiration pick-up device 1 to thereby measure a timing upon switching from an expiratory phase to an inhalatory phase and outputs a trigger signal T at that timing, and an application device 3 that sprays a predetermined amount of a test substance into a nasal cavity or an oral cavity of the experimental animal when the trigger signal T is outputted from the device 2.

12 Claims, 2 Drawing Sheets

(52) U.S. Cl.
CPC ............ *A61M 2016/0024* (2013.01); *A61M 2016/0027* (2013.01); *A61M 2016/0039* (2013.01); *A61M 2205/075* (2013.01); *A61M 2205/10* (2013.01); *A61M 2205/332* (2013.01); *A61M 2205/3368* (2013.01); *A61M 2205/502* (2013.01); *A61M 2209/02* (2013.01); *A61M 2230/42* (2013.01); *A61M 2230/63* (2013.01); *A61M 2250/00* (2013.01)

(58) Field of Classification Search
CPC .. A61M 15/0091; A61M 15/08; A61M 16/00; A61M 16/10; A61M 16/14; A61M 16/16; A61M 16/18; A61M 16/20; A61M 2011/006; A61M 2011/007; A61M 2011/008; A61M 2015/0013; A61M 2015/0015; A61M 2015/0016; A61M 2015/0018; A61M 2015/009; A61M 2015/08
USPC ............ 128/200.14, 200.21–200.23, 203.12, 128/204.18, 204.23, 204.26; 600/529, 600/538
See application file for complete search history.

(56) References Cited

U.S. PATENT DOCUMENTS

| | | | | |
|---|---|---|---|---|
| 4,244,392 A * | 1/1981 | Griswold et al. | ............ | 137/218 |
| 4,649,911 A * | 3/1987 | Knight | .................. | A61M 15/00 |
| | | | | 128/200.21 |
| 4,819,629 A * | 4/1989 | Jonson | .................... | 128/203.22 |
| 4,823,784 A * | 4/1989 | Bordoni | ................ | A61M 15/02 |
| | | | | 128/200.14 |
| 4,827,964 A * | 5/1989 | Guido et al. | .................. | 137/81.1 |
| 5,074,299 A * | 12/1991 | Dietz | ........................ | 128/204.21 |
| 5,080,093 A * | 1/1992 | Raabe et al. | ............. | 128/203.12 |
| 5,235,989 A * | 8/1993 | Zomer | .......................... | 600/534 |
| 5,253,640 A * | 10/1993 | Falb | .................... | G01F 25/0015 |
| | | | | 128/200.24 |
| 5,458,135 A * | 10/1995 | Patton et al. | ............. | 128/200.14 |
| 5,479,920 A * | 1/1996 | Piper et al. | .............. | 128/204.23 |
| 5,613,489 A * | 3/1997 | Miller | ............... | A61M 15/0086 |
| | | | | 128/200.14 |
| 5,713,349 A * | 2/1998 | Keaney | ..................... | 128/204.23 |
| 5,931,159 A * | 8/1999 | Suzuki et al. | ............ | 128/204.18 |
| 6,029,660 A * | 2/2000 | Calluaud et al. | ........ | 128/203.12 |
| 6,412,481 B1 * | 7/2002 | Bienvenu et al. | ....... | 128/200.21 |
| 6,606,989 B1 * | 8/2003 | Brand et al. | ............. | 128/200.16 |
| 6,715,485 B1 | 4/2004 | Djupesland | | |
| 7,353,823 B2 | 4/2008 | Tsutsui | | |
| 7,802,569 B2 * | 9/2010 | Yeates | ............... | A61M 15/0086 |
| | | | | 128/200.14 |
| 7,806,117 B2 | 10/2010 | Tsutsui | | |
| 2005/0217666 A1 | 10/2005 | Fink et al. | | |
| 2007/0018113 A1 | 1/2007 | Gonin et al. | | |
| 2009/0000615 A1 * | 1/2009 | Pohlmann | .............. | A61M 11/06 |
| | | | | 128/200.21 |
| 2010/0004790 A1 | 1/2010 | Harbin, III et al. | | |
| 2010/0043790 A1 * | 2/2010 | Tatarek | .................. | A61M 11/06 |
| | | | | 128/203.14 |

FOREIGN PATENT DOCUMENTS

| | | |
|---|---|---|
| JP | 2005-261770 A | 9/2005 |
| JP | 2001-161819 A | 6/2010 |
| WO | WO 00/21598 A1 | 4/2000 |

\* cited by examiner

TEST SUBSTANCE ADMINISTRATION SYSTEM FOR ANIMAL EXPERIMENT

TECHNICAL FIELD

The present invention concerns a test substance administration system for animal experiment to administer a test substance such as a drug or a chemical through a nose or a mouth of an experimental animal.

BACKGROUND ART

Pernasal administration or inhalative (transpulmonary) administration of a drug by way of a patient's nose or mouth has been adapted generally as an administration method exclusively for local therapy such as therapy of rhimitis or asthma. However such a method has attracted attention in recent years as a method not only for local therapy but also as a method of administering a drug with expected systemic action that has been considered only possible by injection, such as a peptide type drug or an immediate acting drug.

As a method of pernasal administration or inhalative administration, a patient would generally inhale a drug dispensed from an application device such as an applicator or a respiratory gas mixer from a nose or mouth to the site of administration. An administration device proposed by the present applicant is adapted such that when a capsule filled with a predetermined amount of a powder drug is loaded into the device, the capsule is perforated with apertures on both ends thereof, the powder drug in the apertured capsule is driven out by a pressurized air supplied from a rubber pump, etc. and then sprayed from a nozzle inserted into a patient's nasal cavity or oral cavity (refer to Patent Documents 1 and 2).

[Patent Document 1]
JP-A No. 2005-168513
[Patent Document 2]
JP-A No. 2005-261770

By the way, a newly developed effective ingredient in a natural substance or a newly developed chemical synthesis drug require precise determination of its pharmaceutical effects and side effects through pharmacological experiments using experimental animals. Also, when investigating the effect of a chemical on the human body, precise evaluation is required using experimental animals. For this purpose, when screening a new drug with an aim of pernasal administration or inhalative administration, or in such case as investigation of the effect of a chemical in atmospheric air on the inside of a nasal cavity or a lung, it is necessary to administer the drug or the chemical into the nasal cavity or into the lung of experimental animals such that it is uniformly distributed therein. If the test substance is administered such that it is unevenly concentrated in a certain region of the nasal cavity or the lung for a local therapy, it may possibly induce significant local irritation or result in insufficient therapeutic effect. Also such uneven administration for a systemic therapy would reduce the effective surface area of the mucosal membrane that contributes to absorption, which may hinder the confirmation of toxicity that would have been observed ordinarily in human or the confirmation of the absorption ratio or therapeutic effect that would have been attained ordinarily in human.

Particularly, different from human, an experimental animal does not inhale a drug from a nose or a mouth on its own will and, when the body is constrained to carry out the experiment. If the animal is constrained for a long time, breathing may become erratic due to stress. Accordingly, it has been extremely difficult to administer a necessary amount of a test substance such that it is distributed uniformly from the nose or the mouth into the nasal cavity or into the lung thereof.

That is, to precisely evaluate and demonstrate the pharmaceutical effect, side effect, toxicity, etc. of a test substance which is dosed by pernasal administration or inhalative administration into the nasal cavity or into the lung of an experimental animal, it is necessary to administer a necessary amount of the test substances such that it is distributed uniformly into the nasal cavity or into the lung. In the pernasal administration or inhalative administration, the dosage or the distribution of the test substance administered into the nasal cavity or into the lung changes depending on the timing with respect to respiration. If the timing is incorrect, a portion of the test substance may possibly scatter to other locations and the necessary amount of the test substance would not be administered into the nasal cavity or into the lung, or the test substance may become unevenly concentrated in a certain part of the nasal cavity or in the lung. Accordingly, while the test substance has to be administered at an appropriate timing according to the respiratory state of an experimental animal, it is extremely difficult to administer the test substance at a precise timing and this results in a problem that the necessary amount of a test substance cannot be administered reliably.

DISCLOSURE OF THE INVENTION

Subject to be Solved by the Invention

A technical subject of the present invention is to enable administration of a necessary amount of a test substance uniformly and reliably from a nose or a mouth of an experimental animal into the nasal cavity or into the lung thereof.

Means for Solving the Subject

For solving the subject described above, the present invention provides a test substance administration system used for animal experiment that administers the test substance such as a drug or a chemical used for animal experiments from a nose or a mouth of an experimental animal, which includes a respiration monitoring device that monitors the respiration state of an experimental animal detected by a respiration pick-up device, thereby measuring the timing upon switching from an expiratory phase to an inspiratory phase and outputs a trigger signal at that timing, and an administration device that sprays a predetermined amount of a test substance into a nasal cavity or into an oral cavity of the experimental animal when the trigger signal is outputted.

Effect of the Invention

According to the invention, since the respiration state of the experimental animal which is visually difficult to be recognized can be monitored by a respiration monitoring device, and a predetermined amount of a test substance can be sprayed into the nasal cavity or into the oral cavity of the experimental animal by the application device on every switching of the respiration state from the expiratory phase to the inspiratory phase, the sprayed test substance can be reliably inhaled into the nasal cavity or into the oral cavity of the experimental animal together with its inspired gas and administered such that it is distributed uniformly into the nasal cavity or into the lung.

BEST MODE FOR CARRYING OUT THE INVENTION

A best mode for carrying out the invention provides a test substance administration system including a respiration monitoring device that monitors the respiration state of an experimental animal detected by a respiration pick-up device thereby monitoring the timing when the expiratory switches to the inspiratory phase and outputs a trigger signal at that timing, and an application device that sprays a predetermined amount of a test substance into the nasal cavity or into the oral cavity of an experimental animal when the trigger signals is outputted. The application device includes an applicator that sprays the test substance in a dispersible dosage form such as a powder, a solution, or a suspension by a pressurized air, and an air supply mechanism that supplies a pressurized air for spraying the test substance to the applicator when the trigger signal is outputted from the respiration monitoring device.

Further, the applicator of the application device is mounted with a nozzle or a mouthpiece for spraying the test substance into the nasal cavity or into the oral cavity of the experimental animal, and the nozzle or the mouthpiece is provided with a respiration pick-up device for detecting the respiration state of the experimental animal. Then, the air supply mechanism that supplies the pressurized air for spraying the test specimen to the applicator has an air pump such as a rubber pump for pushing out and supplying pressurized air intermittently, and an actuator for driving the air pump, in which the actuator is adapted to be actuated by a trigger signal outputted from the respiration monitoring device, or adapted such that it includes an air circuit for supplying a pressurized air from an air pressure source such as a compressor and an automatic valve for turning the air circuit on and off, and the automatic valve is opened by the trigger signal outputted from the respiration monitoring device.

Further, the respiration pick-up device used herein includes a thermistor type temperature sensor that detects the respiration state due to the temperature difference between an expired gas and inspired gas of the experimental animal, a pressure sensor that detects the respiration state due to the change of pressure in the nozzle or the mouthpiece which is caused by the respiration of the experimental animal, or a combination of the pressure sensor and an airflow sensor that detects the respiration state due to the flow rate of the expired gas of the experimental animal flowing into the nozzle or into the mouthpiece, or an electric resistance type sensor that detects the respiration state due to the change in electric resistance which is caused by expansion and contraction of a conductive rubber wound around the thorax portion or the abdominal portion of an experimental animal whose peripheral length is changed by the respiration of the experimental animal.

Example 1

FIG. 1 is a view showing an example of a test substance administration system according to the invention. The system includes a respiration monitoring device 2 that monitors the respiration state of an experimental animal detected by a respiration pick-up device 1 thereby monitoring the timing when the expiratory phase switches to the inhalatory phase and outputs a trigger signal T at that timing, and an application device 3 that sprays a predetermined amount of a test substance into the nasal cavity or into the oral cavity of an experimental animal when the trigger signal T is outputted from the device 2.

The application device 3 includes an applicator 4 that sprays a test substance having a dispersible dosage form such as a powder, a solution, or a suspension, and an air supply mechanism 5 that supplies pressurized air for spraying the test substance to the applicator 4 when the trigger signal T is outputted from the respiration monitoring device 2. The applicator 4 has a nozzle 6 mounted thereto for spraying the test substance into the nasal cavity or into the oral cavity of the experimental animal.

The air supply mechanism 5 has an air pump 7 for pushing out and supplying a pressurized air intermittently and an electromotive, hydraulic, or pneumatic actuator 8 that drives the air pump 7 such that the actuator 8 is actuated by the trigger signal T outputted from the respiration monitoring device 2 and the pressurized air is supplied from the air pump 7 to the applicator 4. The air pump 7 comprises a rubber pump or an elastic air bag that pushes out internal air by compressive deformation, and the actuator 8 is adapted such that the air pump 7 is collapsed by a pair of movable arms 9a, 9b that reciprocate in a direction closer to and away from each other thereby pushing out the internal air. The pressurized air pushed out from the air pump 7 is supplied through an air pipeline 20 provided with a regulator 19 to appropriately control the air pressure to the applicator 4. The air pump 7 is not restricted only to a rubber pump or an elastic air bag but it may also be a bellows pump, a cylinder pump for pushing out the air in a barrel by a piston rod, etc.

The respiration pick-up device 1 has a pressure sensor 10 for detecting a respiration state due to the change of pressure in the nozzle 6 caused by respiration of an experimental animal when the nozzle 6 attached to the applicator 4 is inserted into the nasal cavity or into the oral cavity of the experimental animal, and an airflow sensor 11 for detecting the respiration state by the flow rate of the inspired gas of the experimental animal that flows into the nozzle 6, in which detection signals from both of the sensors 10, 11 are inputted by way of an interface 12 such as a data logger into the respiration monitoring device 2. Both of the sensors 10 and 11 are attached by way of tubes 13, 14 connected with and branched from the nozzle 6 so as not to hinder the flow path of the test substance sprayed from the nozzle 6 although they may also be attached in the nozzle 6. The respective tubes 13, 14 are provided with orifices 15a, 15b, and check valves 16a, 16b for enabling communication between air in the nozzle 6 and external air, so that an appropriate load can be applied to both of the sensors 10, 11 by respiration of the experimental animal without hindering the respiration thereof.

The respiration monitoring device 2 has a computer 17 that judges the respiration state of the experimental animal based on the data inputted from the respiration pick-up device 1 by using the pressure sensor 10 and the airflow sensor 11 in combination, and a monitor 18 for displaying the respiration state on a screen. The computer 17 measures the phase length between the expiratory phase and the inhalatory phase based on the input data from the pressure sensor 10 and measures the intensity change of the respiration (inspiration) based on the input data from the airflow sensor 11 to thereby judge whether the excitation of the experimental animal has subsided and the respiration is stabilized or not. Then, when the phase length between the expiratory phase and the inspiratory phase has substantially settled constant and the intensity change of respiration (expiration) has also decreased to a stable respiration, it detects the timing at which the respiration is switched from the expiratory phase to the inhalatory phase, and outputs a timing signal T to actuate the actuator 8 of the air supply mechanism 5 at that timing.

Thus, since the test substance is sprayed by the applicator 4 into the nasal cavity or into the oral cavity of the experimental animal when the respiration of the experimental animal switches from the expiratory phase to the inhalatory phase, that is, when the experimental animal inhales breath from the nose or the mouth, the sprayed test substance is carried on the inspired gas and applied efficiently such that the substance is uniformly distributed into the nasal cavity or into the lung.

Example 2

FIG. 2 is a view showing another example of a test substance administration system according to the invention. The constitutions of the system are different from those of the system shown in FIG. 1 in that a temperature sensor is used as the respiration pick-up device 1 to detect the respiration state by the temperature difference between the expired gas and the inspired gas of the experimental animal, and the air supply mechanism 5 of the application device 3 has an air circuit 22 for supplying a pressurized air from an air pressure source 21 such as a compressor to the applicator 4 and an automatic valve 23 such as a solenoid valve for turning the air circuit 22 on and off, and the automatic valve 23 is adapted to be opened by the trigger signal T outputted from the respiration monitoring device 2. Other constitutions are common with those of the system in FIG. 1.

The respiration pick-up device 1 in FIG. 2 is a temperature sensor that utilizes the temperature dependent change of the resistance of a thermistor, in which a thermistor detection portion thereof is mounted to a nasal cavity of the experimental animal, or attached to the nozzle 6 mounted to the applicator 4, and detects the change in resistance due to the temperature difference between the expired gas and the inspired gas of the nasal respiration as a respiration curve plot. Then, the respiration monitoring device 2 measures the timing upon switching from the expiratory phase to the inhalatory phase based on the change of the resistance value due to the temperature difference between the expired gas and the inspired gas detected by the respiration pick-up device 1, and outputs a trigger signal T at that timing.

Further, in the air circuit 22 that supplies the pressurized air from the air pressure source 21 to the applicator 4 has, intervened therein, an air filter 24 for purifying the pressurized air, regulators 25 and 26 for regulating the pressure of the pressurized air, a restriction valve 27 for controlling the flow rate of the pressurized air, a check valve 28, etc.

As the applicator 4 shown in FIG. 1 and FIG. 2, a mouthpiece 29 may be attached as shown in FIG. 3 instead of the nozzle 6, in which the mouthpiece 29 is shaped in the form of a mask covering the mouth or both the mouth and the nose of the experimental animal such that the test substance can be sprayed into the nasal cavity or into the oral cavity of the experimental animal, and is provided with a respiration pick-up device 1 such as a pressure sensor for detecting the respiration state due to the change of pressure in the mouthpiece 29 which is caused by the respiration of the experimental animal.

Further, the respiration pick-up device for detecting the respiration of the experimental animal is not restricted to the temperature sensor that detects the respiration state due to the temperature difference between the expired gas and the inspired gas or the pressure sensor that detects the respiration state due to the change of pressure in the nozzle 6 or the mouthpiece 29 caused by respiration. For example, it may be an electric resistance type sensor that detects the respiration state due to the change in electric resistance which is caused by expansion and contraction of a conductive rubber wound around the thorax portion or the abdominal portion of an experimental animal whose peripheral length changes depending on respiration, etc. Further, the applicator 4 is not restricted to the applicators described in patent documents 1 and 2 that spray the powder by the pressurized air but it may be an applicator that sprays a solution or a suspension by pressurized air.

INDUSTRIAL APPLICABILITY

The present invention enables adequate judgment for the pharmaceutical effect and the side-effect of a new drug in a pharmacological experiment using an experimental animal.

DESCRIPTION FOR REFERENCES

Figure 1:
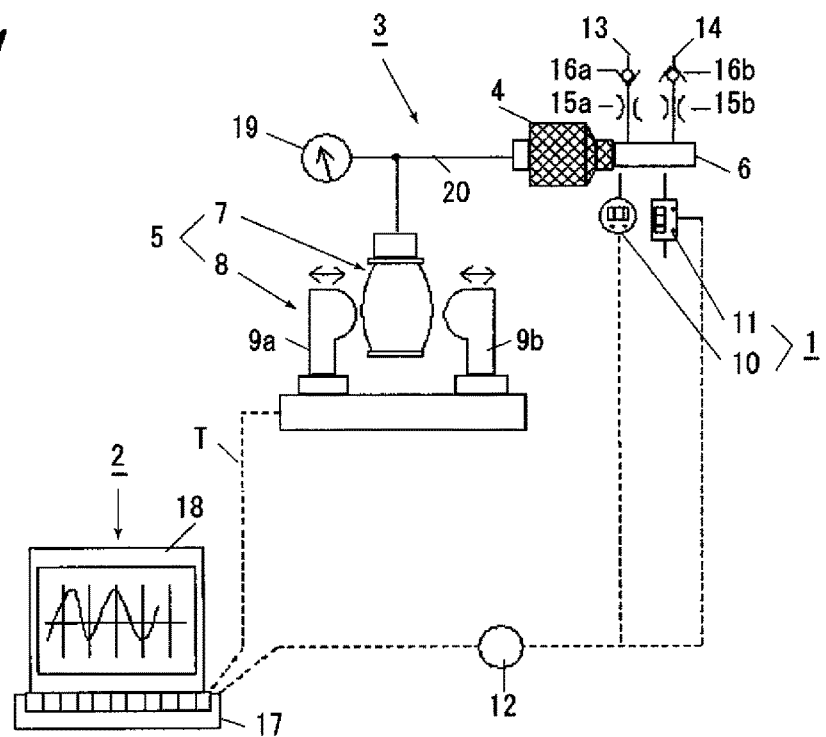
FIG. 1 is a view showing an example of a test substance administration system for animal experiment according to the invention.
Figure 2:
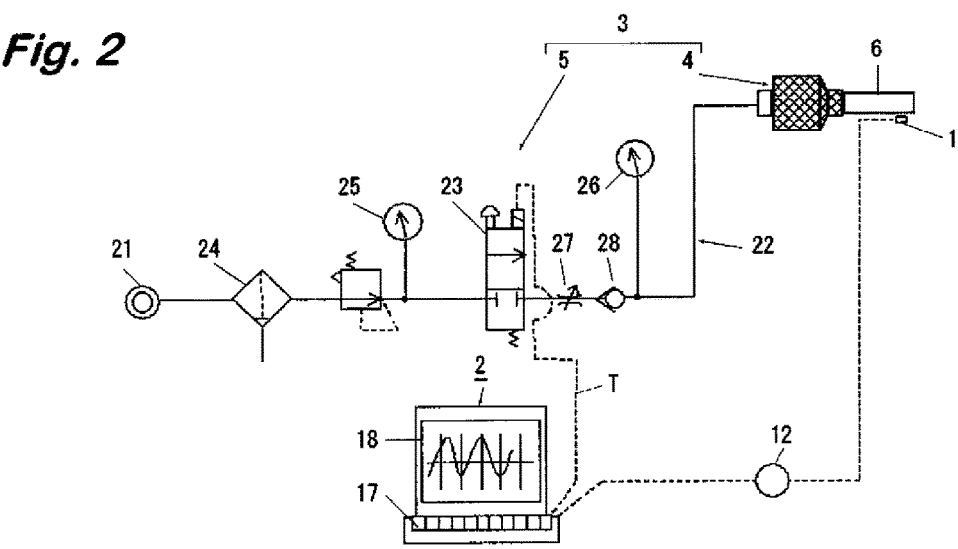
FIG. 2 is a view showing another example of a test substance administration system for animal experiment according to the invention.
Figure 3:
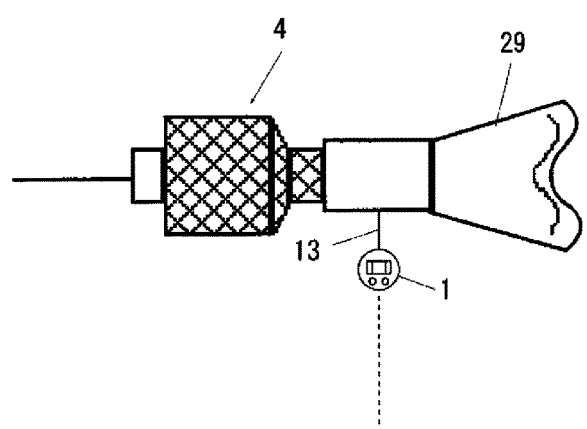
FIG. 3 is a view showing a portion of the constitution of the system according to the invention.

1 respiration pick-up device
2 respiration monitoring device
3 application device
4 applicator
5 air supply mechanism
6 nozzle
7 air pump
8 actuator
10 pressure sensor
11 airflow sensor
12 air pressure source
22 air circuit
23 automatic valve
24 mouthpiece

The invention claimed is:
1. A test substance application system comprising:
a respiration monitoring device that monitors a respiration state of an experimental animal detected by a respiration pick-up device, thereby measuring a timing upon switching from an expiratory phase to an inhalatory phase, and outputs a trigger signal at the timing,
an applicator that is adapted for supplying and actively spraying a predetermined amount of the test substance via a nozzle into a nasal cavity or an oral cavity of the experimental animal when the trigger signal is outputted, wherein the test substance is sprayed as a powder in pressurized air,
wherein the applicator is mounted to the nozzle, and
wherein a longitudinal axis of the nozzle and a longitudinal axis of the applicator align with each other, forming a straight path from the applicator to the nasal cavity or the oral cavity of the experimental animal, an air supply mechanism that supplies the pressurized air only when the trigger signal is outputted, and two check valves connected, each by its own tube, to the nozzle, wherein the tubes are aligned perpendicular to the nozzle and in parallel to each other, wherein the only source of the pressurized air in the test substance application system is the air supply mechanism, and wherein the respiration pick-up device is directly attached to the nozzle.

2. The test substance application system according to claim 1, wherein the air supply mechanism has an air pump that pushes out and supplies the pressurized air intermittently and an actuator for driving the air pump, in which the actuator is actuated by the trigger signal, and wherein the air pump pushes the pressurized air to the applicator through an air pipeline provided with a pressure regulator.

3. The test substance application system according to claim 1, wherein the air supply mechanism has an air circuit that supplies the pressurized air from an air pressure source, and an automatic valve that turns the air circuit to on and off, and wherein the automatic valve is opened by the trigger signal.

4. The test substance application system according to claim 3, wherein the air pressure source is a compressor.

5. The test substance application system according to claim 1, wherein the respiration pick-up device is a temperature sensor that detects the respiration state due to the temperature difference between an expired gas and an inhalation of the experimental animal.

6. The test substance application system according to claim 1, wherein the respiration pick-up device is a pressure sensor that detects the respiration state due to a change of pressure in the nozzle caused by respiration of the experimental animal.

7. The test substance application system according to claim 6, wherein the respiration pick-up device uses the pressure sensor and an airflow sensor that detects the respiration state due to a flow rate of an expired gas of the experimental animal flowing into the nozzle, which are used in combination.

8. The test substance application system according to claim 1, wherein the respiration pick-up device is an electric resistance type sensor that detects a respiration due to a change of an electric resistance value by expansion and contraction of a conductive rubber adapted to a thorax portion or an abdominal portion of the experimental animal whose peripheral length changes depending on the respiration of the experimental animal, and wherein the experimental animal is not a human.

9. The test substance application system according to claim 1, wherein the applicator actively sprays a predetermined amount of the test substance into the nasal cavity of the experimental animal when the trigger signal is outputted.

10. The test substance application system according to claim 1, wherein the test substance application system is for nasal administration and is not for oral administration.

11. The test substance application system according to claim 1, wherein inhalation air is provided only from behind the applicator in an airflow direction towards the nasal cavity of the experimental animal.

12. The test substance application system according to claim 1, wherein the nozzle is adapted to be inserted into the nasal cavity.

* * * * *